United States Patent [19]
Rambach

[11] Patent Number: 6,165,743
[45] Date of Patent: Dec. 26, 2000

[54] **CULTURE MEDIUM FOR REVEALING ENTEROHEMORRHAGIC *E. COLI* BACTERIA AND PROCEDURE THEREFOR**

[76] Inventor: Alain Rambach, 73 boulevard du Montparnasse, 75006 Paris, France

[21] Appl. No.: 09/171,277

[22] PCT Filed: Apr. 14, 1997

[86] PCT No.: PCT/FR97/00656

§ 371 Date: Oct. 14, 1998

§ 102(e) Date: Oct. 14, 1998

[87] PCT Pub. No.: WO97/39103

PCT Pub. Date: Oct. 23, 1997

[30] Foreign Application Priority Data

Apr. 15, 1996 [FR] France .................................. 96 04655

[51] Int. Cl.$^7$ .............................. C12Q 1/10; C12Q 1/34; G01N 33/569; C12N 9/38

[52] U.S. Cl. ............................ 435/38; 435/7.37; 435/18; 435/208

[58] Field of Search .................... 435/252.8, 34, 435/38, 18, 207, 208, 7.72, 209, 7.37, 252.33

[56] References Cited

U.S. PATENT DOCUMENTS

| | | | |
|---|---|---|---|
| 3,562,113 | 2/1971 | Kawamura et al. | 195/66 |
| 4,923,804 | 5/1990 | Ley et al. | 435/38 |
| 5,210,022 | 5/1993 | Roth et al. | 435/34 |
| 5,821,066 | 10/1998 | Pyle et al. | 435/7.2 |

FOREIGN PATENT DOCUMENTS

| | | | |
|---|---|---|---|
| 2 696 476 | 4/1994 | France | . |
| WO 94/08043 | 4/1994 | France | C12Q 1/04 |
| WO 92/02820 | 2/1992 | WIPO | G01N 33/569 |

OTHER PUBLICATIONS

Todd et al. Rapid Hydrophobic Grid Membrane Filter–Enzyme–Labeled Antibody Procedure for Identification and Enumeration of Escherichia Coli 0157 in Foods. Appl. Environ. Microbiol. 54, pp. 2536–2540, (Oct. 1988).

Doyle et al. Isolation of *Escherichia Coli* 0157:H7 From Retail Fresh Meats and Poultry. Appl. Environ. Microbiol. 53, pp. 2394–2396, (Oct. 1987).

Ogdon et al. An Evaluation of Fluorogonic and Chromogenic Assays for the Direct Enumeration of *Escherichia Coli.* Lett. Appl. Microbiol. 13, pp. 212–215, (1991), No Month Found.

Frampton et al. J. Food Protection 51(5), pp. 402–404, (May 1988).

X–a–Gal Medium; 1993 American Society of Brewing Chemists, Inc. pp. 185–187, (1993), No Month Found.

Derwent abstract XP 002020743, AN 92–110005 C14! PN JP4051900 A 920220, abstract only. (Feb. 1992).

*Primary Examiner*—Ardin H. Marschel
*Assistant Examiner*—Marjorie A. Moran
*Attorney, Agent, or Firm*—Blakely Sokoloff Taylor & Zafman LLP

[57] ABSTRACT

The invention concerns a culture medium and a method for revealing enterohemorrhagic *E. coli* bacteria, particularly serotypes O157 and/or O11, comprising a chromogenic substrate compound of the α-galactosidase enzyme. The invention likewise concerns a procedure for revealing enterohemorrhagic *E. coli* bacteria in a sample.

16 Claims, No Drawings

CULTURE MEDIUM FOR REVEALING ENTEROHEMORRHAGIC E. COLI BACTERIA AND PROCEDURE THEREFOR

This is the U.S. national stage entry of PCT application No. PCT/FR97/00656 under 35 U.S.C § 371, filed Apr. 14, 1997.

The present invention relates to a novel medium for isolating and identifying E. coli O157 and/or O11 bacteria, and to a process for revealing them.

Enterohemorrhagic Escherichia coli (EHEC), in particular the serotype O157, has been the cause of most of the cases of food poisoning in the United States, Canada and Europe. In North America, beef (in particular raw beef), beef-based products and unprocessed milk have been involved in these epidemics.

The virulence characteristics of this microorganism, which are identical to those of enteropathogenic E. coli and verotoxinogenic E. coli make this microorganism a major public health problem, since it causes hemorrhagic colitis characterized by sanguinolent diarrhea, and these symptoms may develop into very serious renal complications (hemolytic uremic syndrome).

In recent years, studies have thus been directed toward the rapid detection of EHEC strains in food products (FDA, 8th edition, 1995—Bolton et al., 1995), and more particularly toward specific detection of the serotype O157.

The isolation media of the prior art are:
in particular relatively unselective media, such as sorbitol MacConkey medium, and examination of all the gram-negative and sorbitol-negative bacteria,
antibiotics have occasionally been added with limited success since inhibition of the growth of the desired E. coli O157 can be obtained,
a fluorogenic or chromogenic compound has occasionally been added, which allows elimination of the bacterial colonies containing a β-glucuronidase (essentially typical E. coli).

Most of the strains of Escherichia coli O157 isolated from epidemics do not ferment sorbitol in 24 hours, have no β-glucuronidase activity and do not grow at 45.5° C. Thus, many methods for screening for EHEC strains in clinical or food samples use sorbitol MacConkey agar (SMAC) as primary isolation medium.

The suspected sorbitol-negative colonies are then confirmed as Escherichia coli O157 by biochemical and serological tests.

Among the other media most commonly used, mention is made of:
CT-SMAC: medium derived from SMAC, containing two inhibitors (cefixime and potassium tellurite) which make it more selective, since these compounds inhibit many bacteria which do not ferment sorbitol, such as Proteus spp., Morganella morganii, Providencia spp., Hafnia alvei, etc. A study carried out in 1993 showed that close to 400 strains of EHEC E. coli O157, all of which were cultured on CT-SMAC medium, allowed sorbitol-negative colonies to be revealed.
CR-SMAC: medium derived from SMAC, containing cefixime and rhamnose, for revealing sorbitol-negative, rhamnose-negative colonies.
SMAC+MUG (4-methylhumbelliferyl-β-D-glucuronide), for revealing sorbitol-negative, β-glucuronidase-negative colonies.
SMAC+BCIG (5-bromo-4-chloro-3-indoxyl-D-β-glucuronide), for revealing sorbitol-negative, β-glucuronidase-negative colonies.
Fluorocult E. coli O157:H7 agar: medium containing sorbitol, MUG and sodium thiosulfate, for revealing sorbitol-negative, MUG-negative and $H_2S$-negative colonies.

The variants of SMAC medium, which to begin with is a relatively unselective medium, were prepared by adding inhibitors, which contribute toward increasing the sensitivity of isolation of E. coli O157 by eliminating the associated flora.

However, the current detection techniques have major drawbacks, as regards both the sensitivity and the specificity, since E. coli O157 is present in low amount in food samples, compared with the other microorganisms present, and compared with other species such as E. hermanii which has the same phenotypes on the current media.

The present invention provides a solution to this problem since it provides better specificity and selectivity than those of the media of the prior art, since the addition to a colorless medium of chromogen which detects the β-galactosidase enzyme allows the strains of serogroup O157 and often those of serogroup O11 to be detected rapidly and easily. Highly concentrated colorations are obtained, the color of which depends on the chromophoric part of the chromogen chosen, these colorations being localized in the colonies and allowing easy revelation.

The present invention thus relates to a novel culture medium for revealing enterohemorrhagic E. coli bacteria, in particular of the serotypes O157 and/or O11, which comprises, besides a culture medium for E. coli, a chromogenic compound which is a substrate for the α-galactosidase enzyme.

In order to increase the selectivity, a chromogenic compound which is a substrate for P-glucosidase can be added, which in particular eliminates a large number of coliform bacteria.

In order to increase the selectivity, a chromogenic compound which is a substrate for β-glucuronidase can be added, which in particular allows most of the E. coli of the serogroups other than O157 and O11 to be eliminated.

Advantageously, the chromogenic compound which is a substrate for the α-galactosidase enzyme is chosen from indoxyl-α-galactoside derivatives, in which the chromophore is chosen from substituted or unsubstituted indoxyl radicals.

Preferably, the chromogenic compound which is a substrate for α-glucosidase is chosen from indoxyl-β-glucoside derivatives, in which the chromophore is chosen from substituted or unsubstituted indoxyl radicals.

The chromogenic compound which is a substrate for β-glucuronidase is preferably chosen from indoxyl-β-glucuronide derivatives in which the chromophore is chosen from substituted or unsubstituted indoxyl radicals.

The term substituted or unsubstituted indoxyl is understood to refer to indoxyl radicals and indoxyl radicals substituted with one or more alkyl or halogen radicals. They are more particularly alkyl, halo, dihalo or trihalo indoxyl radicals, preferably chosen from bromoindoxyl, chloroindoxyl, dichloroindoxyl, chlorobromoindoxyl, trichloroindoxyl and methylindoxyl radicals.

Advantageously, the indoxyl chromophoric compounds are chosen from 3-indoxyl, 6-chloroindoxyl, 5-bromoindoxyl, 3-bromoindoxyl, 4,6-dichloroindoxyl, 6,7-dichloroindoxyl, 5-bromo-4-chloroindoxyl, 5-bromo-6-chloroindoxyl and 4,6,7-trichloroindoxyl radicals.

Preferably, the chromogenic compound which is a substrate for the α-galactosidase enzyme is chosen from the following compounds:

5-bromo-6-chloro-3-indoxyl-α-galactoside, and
6-chloro-3-indoxyl-α-galactoside.

For the chromogenic compounds which are substrates for the β-glucosidase and/or β-glucuronidase enzymes, the chromophore is preferably chosen from the following radicals:
5-bromo-4-chloro-3-indoxyl,
5-bromo-3-indoxyl, and
3-indoxyl.

Advantageously, the medium according to the invention comprises between 0.01 and 0.2 g/l of chromogen which is a substrate for α-galactosidase, preferably about 0.05 g/l.

Where appropriate, the concentration of chromogenic compounds which are substrates for β-glucosidase and/or β-glucuronidase is also between 0.01 and 0.2 g/l, preferably about 0.05 g/l.

Other characteristics of the media according to the invention will become apparent in the light of the examples below.

EXAMPLE 1

| CHROMagar O157 formulation | in g/l |
|---|---|
| agar | 15 |
| peptone | 5 |
| yeast extract | 2 |
| meat extract | 1 |
| NaCl | 5 |
| 5-bromo-6-chloro-3-indoxyl-α-galactoside | 0.05 |
| 5-bromo-4-chloro-3-indoxyl-β-glucoside | 0.05 |
| 5-bromo-4-chloro-3-indoxyl-β-glucuronide | 0.05 |
| deoxycholate | 0.5 |

EXAMPLE 2

Colorations Obtained by Various Strains

The culture medium is inoculated with various bacterial strains and is then left to incubate for 24 hours.

|  | MacConkey sorbitol | CHROMagar O157 |
|---|---|---|
| Coliforms | red | Blue |
| E. coli typical | red | Blue |
| E. coli O157 | colorless | Violet |
| E. hermanii | colorless | colorless |
| Hafnia alvei | colorless | colorless |
| Proteus mirabilis | colorless | colorless |
| Pseudomonas | colorless | colorless |

Even strains of E. coli O157 which are, however, SLT+ (Shigella Like Toxin positive) with the sorbitol-positive nature and which are revealed by the medium of the invention are found, whereas they are falsely negative, which are red on sorbitol MacConkey medium, and thus missed. The medium of the invention thus not only provides a specificity advantage (elimination of false positives) but also provides a sensitivity advantage (detection of falsely negative strains on sorbitol MacConkey medium), which is very important.

Furthermore, the medium of the invention gives a good yield of growth since, except for the elective manner for inhibiting the gram-positive bacteria, the medium is not based mainly on a principle of selective growth.

The present invention also relates to a process for revealing enterohemorrhagic E. coli in a sample, in which the culture medium according to the invention is inoculated with the sample or an inoculum of the said sample, after which the presence, if any, of enterohemorrhagic E. coli is revealed.

In the field of food microbiology, it is desired, for example, to demonstrate that there are less than ten E. Coli O157:H7 bacteria in a food. A method for microbial growth is used, optionally followed by a method of immunouptake enrichment IMS before plating out, using antibodies anchored to beads. However, this enrichment does not eliminate several bacteria which give false positive results on the media of the prior art. The use of the media according to the invention thus provides a crucial advantage even when this immunouptake enrichment IMS method is used.

What is claimed is:

1. A process for detecting and differentiating enterohemorrhagic E. coli (EHEC) bacteria in a sample comprising:
   inoculating a culture medium with the sample or with inoculum derived from the sample, the culture medium comprising:
   a) a chromogenic compound which is a substrate for α-galactosidase, and
   b) at least one of a chromogenic compound which is a substrate for β-glucuronidase and a chromogenic compound which is a substrate for β-glucosidase; and
   detecting the presence of EHEC on the culture medium; by
   comparing the coloration of all microorganisms on the culture medium.

2. The process of claim 1, wherein the chromogenic compound which is a substrate for α-galactosidase is an indoxyl α-galactoside having a chromophore selected from the group consisting of substituted indoxyl radicals and unsubstituted indoxyl radicals.

3. The process of claim 2, wherein the chromogenic compound which is a substrate for α-galactosidase is selected from the group consisting of 5-bromo-6-chloro-3-indoxyl-α-galactoside and 6-chloro-3-indoxyl-α-galactoside.

4. The process of claim 1, wherein the culture medium comprises a chromogenic compound which is a substrate for β-glucuronidase and a chromogenic compound which is a substrate of β-glucosidase.

5. The process of claim 1, wherein the chromogenic compound which is a substrate for the β-glucosidase is selected from the group consisting of indoxyl-β-glucoside and the chromogenic compound which is a substrate for the β-glucuronidase is selected from the group consisting of indoxyl-β-glucuronide, and the chromophore(s) of the chromogenic compound(s) is (are) selected from the group consisting of substituted indoxyl radicals and unsubstituted indoxyl radicals.

6. The process of claim 5, wherein the chromophore of the chromogenic compound which is a substrate for an enzyme selected from the group consisting of β-glucosidase, β-glucuronidase and any combination thereof is selected from the group consisting of 5-bromo-4-chloro-3-indoxyl, 5-bromo-3-indoxyl, 3-indoxyl and any combination thereof.

7. The process of claim 1, wherein the concentration of the chromogenic compound which is a substrate for a-galactosidase is approximately in the range of 0.01 and 0.2 g/l.

8. The process of claim 1, wherein the concentration of the chromogenic compound which is a substrate for α-galactosidase is about 0.05 g/l.

9. The process of claim 1 wherein the concentration of the chromogenic compound(s) which is (are) a substrate for an enzyme selected from the group consisting of β-glucuronidase, β-glucosidase and any combination thereof, is approximately in the range of 0.01 and 0.2 g/l.

10. The process of claim 1, wherein the concentration of the chromogenic compound(s) which is (are) a substrate for an enzyme selected from the group consisting of β-glucuronidase, β-glucosidase and any combination thereof, is about 0.05 4 g/l.

11. The process of claim 1, wherein the chromophores for each of the chromogenic compounds are selected from the group consisting of indoxyl radicals substituted with one or more alkyl radicals, indoxyl radicals substituted with one or more halogen radicals.

12. The process of claim 11, wherein the indoxyl radicals are selected from the group consisting of bromoindoxyl, chloroindoxyl, dichloroindoxyl, chlorobromoindoxyl, trichloroindoxyl, methylindoxyl, and any combination thereof.

13. The process of claim 1, wherein the EHEC is selected from the group consisting of serotype O157 and serotype O11.

14. The process of claim 1, wherein the sample is subjected to a method of microbial growth before innoculation.

15. The process of claim 14, wherein said method of microbial growth is followed by a method of immunouptake enrichment IMS before inoculating the culture medium.

16. A process for differentiating enterohemorrhagic *E. coli* (EHEC) bacteria from other microorganisms in a sample, comprising:

inoculating a culture medium with the sample or with inoculum derived from the sample, the culture medium comprising:
  a) a chromogenic compound which is a substrate for α-galactosidase, and
  b) at least one of a chromogenic compound which is a substrate for β-glucuronidase and a chromogenic compound which is a substrate for β-glucosidase;

detecting the presence of EHEC on the culture medium; and differentiating EHEC from the other microorganisms in said sample by comparing the coloration of all microorganisms on the culture medium.

* * * * *

UNITED STATES PATENT AND TRADEMARK OFFICE
CERTIFICATE OF CORRECTION

PATENT NO.    : 6,165,743
DATED         : December 26, 2000
INVENTOR(S)   : Rambach It is certified that error appears in the above-identified patent and that said Letters Patent is hereby corrected as shown below:

Column 4, claim 7,
Line 61, delete "a-galactoisidase" and insert -- α-galactosidease --.

Column 5, claim 10,
Line 8, delete "0.05 4 g/l" and insert -- 0.05 g/l --.

Signed and Sealed this

Eleventh Day of December, 2001

*Attest:*

NICHOLAS P. GODICI
*Attesting Officer*    Acting Director of the United States Patent and Trademark Office

UNITED STATES PATENT AND TRADEMARK OFFICE
CERTIFICATE OF CORRECTION

PATENT NO. : 6,165,743
DATED : December 26, 2000
INVENTOR(S) : Rambach

It is certified that error appears in the above-identified patent and that said Letters Patent is hereby corrected as shown below:

<u>Column 4,</u>
Line 61, delete "a –galactoisidase" and insert -- α-galactosidase --.

<u>Column 5,</u>
Line 8, delete "0.05 4 g/l" and insert -- 0.05 g/l --.

Signed and Sealed this

Thirtieth Day of March, 2004

JON W. DUDAS
*Acting Director of the United States Patent and Trademark Office*